(12) United States Patent
Lauto et al.

(10) Patent No.: US 6,323,037 B1
(45) Date of Patent: Nov. 27, 2001

(54) COMPOSITION FOR TISSUE WELDING AND METHOD OF USE

(75) Inventors: Antonio Lauto, New York; Dix P. Poppas, Larchmont, both of NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/287,383

(22) Filed: Apr. 6, 1999

Related U.S. Application Data

(60) Provisional application No. 60/080,830, filed on Apr. 6, 1998.

(51) Int. Cl.$^7$ .................................................. G01N 33/00
(52) U.S. Cl. ............................. 436/86; 436/518; 606/8; 424/426; 424/428; 530/300
(58) Field of Search ........................... 606/2, 8, 40, 213, 606/214, 215; 424/423, 426–428; 436/86, 518, 88; 128/898; 623/1; 530/300, 530

(56) References Cited

U.S. PATENT DOCUMENTS

| | | |
|---|---|---|
| 5,209,776 | 5/1993 | Bass et al. . |
| 5,292,362 * | 3/1994 | Bass et al. ........................... 106/124 |
| 5,334,191 | 8/1994 | Poppas et al. . |
| 5,552,452 | 9/1996 | Khadem et al. . |
| 5,662,712 * | 9/1997 | Pathak et al. ........................... 623/12 |
| 5,713,891 | 2/1998 | Poppas . |
| 5,948,427 * | 9/1999 | Yamamoto et al. .................. 424/426 |
| 6,087,552 * | 7/2000 | Gergory ................................ 623/11 |

FOREIGN PATENT DOCUMENTS

| | | |
|---|---|---|
| WO 91/04073 | 4/1991 | (WO) . |
| WO 96/07356 | 3/1996 | (WO) . |
| WO 96/22054 | 7/1996 | (WO) . |
| WO 96/38093 | 12/1996 | (WO) . |

OTHER PUBLICATIONS

Poppas et al., "Preparation of Human Albumin Solder for Laser Tissue Welding", Laser in Surgery and Medicine 13:577–580, 1993.*
Poppas et al., *J. Urol.*, 150: 648–650 (1993).
Poppas et al. *J. Urol.*, 150: 1052–1055 (1993).
Poppas et al., *Lasers in Surg. & Med.* 13: 577–580 (1993).
Poppas et al., *J. Urol.*, 139: 415–417 (1988).
Poppas et al., *Contemporary Urology*, 23–32 (1993).
Poppas et al., *Urology* 45(2): 253–257 (1995).
Friedmann, *Scientific American*, 96–105 (Jun. 1997).
Lauto et al., *Lasers in Surgery and Medicine*, 23 (5), 258–262 (1998).
Poppas et al., *Lasers in Surgery and Medicine*, 19, 2–8 (1996).
Poppas et al., *Lasers in Surgery and Medicine*, 19, 360–368 (1996).

* cited by examiner

*Primary Examiner*—John Mulcahy
*Assistant Examiner*—Ahmed Farah
(74) *Attorney, Agent, or Firm*—Leydig, Voit & Mayer, Ltd.

(57) ABSTRACT

A composition for tissue welding is provided. The composition comprises an active compound, a solvent, and an energy converter and is insoluble in physiological fluids. A method for welding a tissue is also provided. The method comprises contacting a tissue with the above composition and exciting the composition such that the tissue becomes welded.

15 Claims, No Drawings

COMPOSITION FOR TISSUE WELDING AND METHOD OF USE

This application claims benefit of Prov. No. 60/080,830 filed Apr. 6, 1998.

TECHNICAL FIELD OF THE INVENTION

The present invention relates to a composition and a method for tissue welding.

BACKGROUND OF THE INVENTION

Traditional methods for closing tissue wounds or incisions include the use of sutures, clips, or staples. While such techniques are generally adequate in sealing tissue wounds or incisions, they have associated problems that limit their use. For example, the use of sutures, clips or staples in closing tissue wounds can often lead to scar formation, infection, and a multitude of immunological responses. Tissue incompatibility with sutures, clips, or staples may cause fistulas, granulomas, and neuromas that can be painful and difficult to treat. Sutures, clips, or staples may also tend to cut through weak parenchymatous or poorly vascularized tissue. Additionally, sutures leave behind a tract that can allow for leakage of fluids and can provide a convenient entry point for a variety of organisms.

The success of traditional methods in sealing tissue wounds or incisions also is very dependent on the skill of the practitioner performing such methods. The manual dexterity and eyesight of the practitioner impose severe limits on the use of sutures, staples, and clips, especially when microsurgery is being performed.

An alternative to traditional methods for sealing tissue wounds or incisions is the use of compositions suitable for tissue welding. By "tissue welding" it is meant that an energy source is used to excite the composition, which results in the sealing or closure of the tissue wound or incision. Typically, a tissue welding composition will be applied to the area of the tissue that requires sealing. Upon excitation by an energy source, the composition fuses to the tissue, and the bonding between the composition and the tissue allows the severed parts of the tissue to be proximal to each other, much in the same way as when sutures, staples, or clips are used. Such tissue welding compositions are absorbable within a few weeks and, therefore, do not cause tissue scar formation.

Despite the general advantages that tissue welding has over the more traditional methods, current compositions used in tissue welding suffer from numerous drawbacks. Compositions presently in use solubilize in physiological fluids after application and before excitation by an energy source. Blood dilution of the composition after application, but before excitation, alters the shape and rigidity of the composition as it existed when the composition was applied to the tissue. Such alterations to the shape and rigidity of the composition prior to excitation change the energy absorption characteristics of the composition and weaken its repair tensile strength. The result is an impairment of the reliability and reproducibility of the tissue welding technique.

In view of the foregoing problems, there exists a need for a tissue welding composition that is not soluble or has a low solubility in physiological fluids prior to excitation by an energy source. The present invention provides such a composition and a related method of use. These and other advantages of the present invention, as well as additional inventive features, will be apparent from the description of the invention provided herein.

BRIEF SUMMARY OF THE INVENTION

The present invention provides a physiological fluid-insoluble composition for tissue welding comprising an active compound, a physiologically compatible solvent and an energy converter. The present invention also provides a method for welding a tissue comprising (a) contacting tissue with a physiological fluid-insoluble composition comprising an active compound, a physiologically compatible solvent, and an energy converter, and (b) exciting the composition such that the tissue becomes welded.

The invention may best be understood with reference to the following detailed description of the preferred embodiments.

DESCRIPTION OF THE PREFERRED EMBODIMENTS

The present invention provides a composition for tissue welding and a method for welding a tissue. The present inventive composition comprises an active compound, a physiologically compatible solvent, and an energy converter, wherein the active compound is present in the composition in such a concentration that the composition is insoluble in physiological fluids. The present invention also provides a method for welding a tissue comprising (a) contacting tissue with a composition comprising an active compound, a physiologically compatible solvent, and an energy converter, wherein the active compound is present in the composition in such a concentration that the composition is insoluble in physiological fluids, and (b) exciting the composition such that the tissue becomes welded.

By the term "insoluble," it is meant that the composition is insoluble or has a low solubility in water or in other physiological fluids. A composition that is insoluble or has a low solubility will substantially retain its structural properties (i.e., its shape and rigidity) in water or in other physiological fluids, preferably, at a temperature of about 20° C. to about 50° C. for at least about 5 minutes, more preferably, at a temperature of about 25° C. to about 45° C. for at least about 5 minutes, and, most preferably, at a temperature of about 25° C. to about 40° C. for at least about 5 minutes.

The active compound can be any suitable, safe and efficacious organic substance that imparts to the composition the desired degree of insolubility and that allows the composition to bond or fuse to animal tissue, e.g., human tissue. Furthermore, the active compound can be any combination of any suitable organic substances. Preferably, the active compound is a protein or peptide; more preferably, the active compound is selected from the group consisting of albumin, collagen, myoglobin and fibrinogen; and most preferably, the active compound is albumin.

The concentration of the active compound is such that the composition will have the desired degree of insolubility. Thus, the active compound concentration will vary as a function of the type of active compound and the type and concentration of solvent of which the composition is composed. When the active compound is albumin, the active compound concentration is, preferably, equal to or greater than about 70% (w/w), more preferably, than about 75% (w/w), in a physiologically compatible solvent.

In order to achieve high concentrations of active compound in the composition, any suitable physical, chemical or mechanical process can be utilized, particularly, mechanical compression, thermal treatment, irradiation, various chemical treatments, combinations thereof, and the like. Whatever means of combining the active compound and solvent are chosen, the resulting combination is, preferably, homogeneous.

While any suitable solvent can be used in the context of the present invention, the solvent is such that the composition has the desired degree of insolubility in physiological fluids. Preferably, the solvent is such that it sufficiently solvates the active compound without completely dissolving the active compound. More preferably, the solvent is water (e.g., $H_2O$ or $D_2O$) because water can function both as a solvent with respect to albumin and as an energy converter. The choice of solvent depends on the concentration of the solvent and the type and concentration of the active compound utilized.

The concentration of the solvent is such that the composition will have the desired degree of insolubility in physiological fluids and will vary as a function of the type of solvent and the type and concentration of the active compound of which the composition is comprised. Preferably, the concentration of the solvent is such that the active compound is not completely dissolved. When the active compound is albumin, the sum of the concentrations of the solvent and the energy converter is preferably less than about 25% (w/w). In most cases, the concentration of the solvent will be greater than the sum of the concentrations of the energy converter, when the energy converter is different from the solvent, and any bioactive agents, if present, but will be less than the concentration of the active compound.

The energy converter can be any suitable substance that absorbs energy from an energy source and causes the composition to bond or fuse to the tissue. The energy converter can be the same or different than the solvent. Preferably, the energy converter and the solvent are the same, i.e., the solvent also acts as the energy converter. Preferably, the energy converter is selected from the group consisting of water, carbon, carbon black, india ink, iron oxide, indocyanine green, fluorescein, fluorescein isothiocyanate, FD&C Red #40, FD&C Yellow #6, methylene blue, flavins such as riboflavin, xanthenes such as erythrosin and rose bengal, thiazines, and porphyrins such as protoporphyrin IX, uroporphyrin, and hematoporphyrin derivatives. More preferably, the energy converter is carbon black, which is present in a concentration of about 0.15% to about 0.25% (w/w), or water. Most preferably, the energy converter is water.

The concentration of the energy converter depends on the type of energy converter used, the type of energy source used to excite the energy converter, and the type and concentration of the active compound.

Any suitable energy source can be used to excite the composition such that the tissue becomes welded. Preferably, the energy source emits electromagnetic radiation (e.g., laser energy and radiofrequency energy). Preferred laser sources include Nd:YAG lasers, GaAlAs lasers, Argon lasers and $CO_2$ lasers.

Any suitable bioactive agent can be added to the composition either before excitation by an energy source or after welding of the tissue has already occurred. Suitable bioactive agents are variously described in U.S. Pat. No. 5,713, 891 (Poppas). Preferably, the bioactive agent is a protein, a polysaccharide, a nucleic acid, a vitamin, a metal or an ion (e.g., calcium, sodium and potassium), a delivery vehicle for proteins and/or nucleic acids (e.g., a virus and a liposome), or any combination thereof. Furthermore, the nucleic acid can be, for example, a cDNA encoding a protein, an antisense oligonucleotide,or a catalytic RNA. Depending on the sequence of the cDNA and the vehicle used to deliver the cDNA into the target cells, the cDNA, once delivered into the target cells, can either integrate into the target cells' genome or exist within the target cells without integrating into the target cells' genome. Nuclear targeting signals also can be attached to cDNA in order to direct the cDNA to the targeted cells' nuclei and, therefore, raise the effective concentration of the nuclear cDNA. More preferably, the bioactive agent is an enzyme, an enzyme inhibitor, a hemostatic agent, a growth factor, an angiogenic factor, a growth effector molecule, a bacteriostat, a bactericidal factor, an anti-inflammatory agent, a chemotherapeutic agent, an anti-angiogenic agent, a virus, a liposome, or a vitamin.

Preferred growth effector molecules are growth factors and extracellular matrix molecules. Preferred growth factors include epidermal growth factor (EGF), platelet-derived growth factor (PDGF), transforming growth factors (e.g., TGFα, TGFβ), hepatocyte growth factor, heparin binding factor, insulin-like growth factor I or II, fibroblast growth factor (FGF), vascular endothelial growth factor (VEGF), erythropoietin, nerve growth factor, bone morphogenic proteins and muscle morphogenic proteins. Preferred extracellular matrix molecules are fibronectin, laminin, collagens and proteoglycans. Preferred hemostatic agents are thrombin, Factor Xa, fibrinogen and calcium ions. Preferred bacteriostatic and bactericidal agents are antibiotics and other compounds used for preventing or treating infection in wounds.

The composition can also undergo either physical or chemical treatment (e.g., ultra-violet, x-ray, or gamma irradiation) prior to excitation so as to lower, with respect to a given energy converter, the amount of energy that must be absorbed by the composition in order to induce bonding of the composition to the tissue. As a result, the temperature during the tissue weld can be controlled. Such physical and chemical treatments are well-known in the art.

Additionally, the composition can undergo reversible or partially reversible physical or chemical treatments in order to improve the malleability of the composition, alter the composition's ability to form various shapes, or alter the composition's mechanical properties. For example, a composition with a high concentration of albumin can be hydrated to increase its flexibility and malleability. Subsequently, the composition can be molded into the most suitable shape and dehydrated so that the composition can assume its original state. The solid albumin solder also can be exposed to warm water vapor to increase the solder elasticity.

Once the composition has been produced, it can be formed into a shape that best suits the tissue to be repaired. Therefore, for example, the composition can be preformed into a cylindrical shape prior to application to the tissue so that it better fits different anastomoses (i.e., the cylindrical composition can be used to rejoin a severed blood vessel by either being placed inside the vessel or by being placed over the outer surface of the blood vessel). By conforming the shape of the composition to the shape of the tissue to be welded, the tensile strength of the weld will be enhanced.

In addition to manipulating the shape of the composition, multiple compositions can be administered. By "multiple compositions" is meant two or more compositions, which can comprise different active compounds, solvents, and energy converters. In this regard, multiple compositions can be administered in any suitable manner in any suitable configuration. For example, the multiple compositions can be layered. In this regard, the layers can be parallel to each other, of the same or different thickness, which can be uniform or nonuniform for a given composition, i.e., flat, wavy or irregular; etc. Also in this regard, the multiple compositions can be administered in such a manner as to achieve a mixture of compositions, e.g., interspersed globules. Desirably, the multiple compositions are administered in such a manner that multiple layers are applied to the tissue to be welded. Such multiple compositions can be formed either prior to application to the tissue, or, alternatively, each composition can be applied directly to the tissue, e.g., one on top of the other. One advantage of the multiple composition system is that each composition can comprise a bioactive compound. Through the formation of such multiple compositions, it is possible to control the time and rate that the bioactive compound affects the tissue. Another advantage found in multiple layer solder is the lowered laser intensity required to weld the tissue. Multiple layers also provide a new method of measuring the solder-tissue temperature.

Any suitable tissue can be welded utilizing the present inventive solder composition and method. Preferably, the tissues soldered are of the gastrointestinal system (i.e., mouth, pharynx, esophagus, stomach, intestines, salivary glands, pancreas, liver, gallbladder), urinary system (i.e., kidneys, ureters, urinary bladder, urethra), circulatory system (i.e., heart, blood vessels or blood), respiratory system (i.e., nose, pharynx, larynx, trachea, bronchi, bronchioles, lungs), nervous system (i.e., brain and spinal cord, and special sense organs such as the eye) and integumentary system (i.e., skin). Even more preferably, the tissue being targeted is selected from the group consisting of urinary bladder, heart, blood vessel, lung, liver, gallbladder, and eye cells. The solder can also be applied to the tissue in any suitable manner. Suitable tissues and methods of application are variously described in U.S. Pat. No. 5,713,891 (Poppas).

The above-described composition and method for tissue welding are further described in the following examples. These examples serve to illustrate further the present invention and are not intended to limit the scope of the invention.

EXAMPLES

Example 1

This example demonstrates the ability of the present inventive composition to retain its shape over time, according to the method in Antonio Lauto et al., Solubility Study of Albumin Solders for Laser Tissue-Welding, 23 Lasers in Surgery and Medicine 258–262 (1998).

Lyophilized bovine serum albumin (BSA) was reconstituted with distilled water in four different concentrations (56%, 66%, 70%, 75% (w/w)) in order to form compositions suitable for tissue welding.

Each composition was reduced to a fixed thickness film with a parallel plate vice. A rectangular portion of each film was cut with a surgical blade, and each portion was weighed by a digital balance. The weight of each of the four samples was 1.4±0.2 mg, and the thickness of each sample was 0.17±0.02 mm, as measured by digital calipers.

After preparation, the samples were placed in 0.5 ml of a saturated saline solution, and the solution was shaken every minute for 2 or 3 seconds. Every few seconds the portion of the composition samples that was not yet dissolved was rescued and observed under a dissecting microscope at fifty times magnification. The 56% composition was completely dissolved after only 3 minutes. The 66% composition was observed to lose its shape and was observed to curl severely and fold after 45 seconds. The 70% composition lost its shape and severely twisted and curled after only 85 seconds. In addition, both the 66% and 70% compositions broke very easily when they were pulled apart with fine forceps, as observed under the microscope. The 75% composition, surprisingly, retained its shape and twisted only slightly after 50 minutes in solution. Furthermore, the 75% composition was appreciably more resistant to being pulled apart with fine forceps than were the lower concentration compositions.

Example 2

This example demonstrates the improved efficiency of a multiple layer solder. This example further demonstrates the use of multiple layer solder to measure the solder-tissue temperature during welding. See Antonio Lauto et al., Two-layer film as a Laser Soldering Biomaterial, submitted to Lasers in Surgery and Medicine.

One solder layer (white layer) contained 72% BSA and distilled water (by weight), and the other layer (black layer) contained 72% BSA, 0.25%±0.06% or 0.39%±0.08% carbon black (CB) and distilled water. The thickness of the white layer and the black layer was approximately half the total film thickness (0.110–0.150 mm). Each layer of the film was reduced to a fixed thickness film with a parallel plate vice. A rectangular portion of each film was then cut into strips with a surgical blade.

A diode laser ($\lambda$=810 nm), at a constant irradiation dose, was used in conjunction with the protein strips to weld sections of dog small intestine (approximately 2×0.7 cm). All the tissue repairs were performed under an operating microscope at 20× magnification. The tissue was harvested the same date of the laser repair. These sections were cut along the middle line and repaired end-to-end with the two-layer solder (TL solder) or with the black one-layer solder (OL solder). Two strips (dimensions approximately 3.5×0.6×015 mm) were positioned across the intestine middle incision. The strips were partially dissolved by the tissue moisture, but still retained their shape. As the strip was lasered, the liquefied part of the solder was welded to the serosa. A silica optical fiber (core diameter=400 $\mu$m) delivered the beam in a continuous wave onto the solder with a spot size of approximately 500 $\mu$m. The black layer of the TL solder was positioned onto the tissue to absorb the laser beam and efficiently transmit the generated heat to the tissue-solder interface.

The soldered intestine was tested acutely to assess the strength of the repair by using a calibrated tensiometer (Instrom Mini 55, MA), interfaced with a personal computer. The specimen was clamped to the tensiometer by pneumatic grips, which moved 22 mm/min until the solder weld failed, by separating the two intestine segments. The tissue was kept wet throughout the procedure, since the tensile strength increased by drying. The breaking force was recorded. Three welds were performed in each group for histological evaluation. The samples were fixed in formalin and stained with Hematoxylin or Masson's Trichrome.

To assess the laser attenuation in the solder, a spectrophotometer (Shimadzu UV-1201) measured separately the absorbance (accuracy and repeatability=±0.007) of the black and white solder film at 810 nm (resolution=5±0.5 nm). The extinction length (90% of laser attenuation) was then calculated from the solder absorbance.

There was no significant difference ($p>0.05$) between the breaking force of the TL and OL solder repairs when the thickness of the solder strips was approximately 0.15±0.01 mm. The OL solder performed stronger repairs than the TL solder (p+0.03) when the thickness of the solder strips was approximately 0.1±0.01. The OL solder suffered disruption and ablation on its top, where many air bubbles were localized. In contrast, the TL solder preserved its structure almost completely, although some air bubbles were localized in the solder middle plane and on both layers. Abundant black fumes were observed during the laser welding of the OL solder, while almost no fumes were present with TL solder repairs. The tensile strengths of the OL and TL solders were similar when laser power and energy dose were kept constant.

Less laser intensity (W/cm$^2$) was required on the black layer for the TL solder repairs. In these repairs, the laser path was increased by half solder thickness (the white layer) prior to the CB absorption, demonstrating less laser intensity. The laser-generated heat diffused only half thickness before reaching the solder tissue interface, while the heat had to diffuse the whole thickness to weld the OL solder to the tissue. The OL solder suffered laser vaporization, ablation and sometimes carbonization of its top. The TL solder remained intact after irradiation as the laser intensity on the black layer decreased by beam divergence and scattering. Therefore, the multiple (i.e., two) layer solder was more efficient at tissue welding than the one layer solder.

In addition, one strip of solder was welded onto extra sections of intestine, as described above. The strips comprised one or two layers and their dimensions were approximately 3.5×0.8×0.15 mm. The temperature of the lasered solder surface and of the solder-tissue interface was measured by two K-type thermocouples during laser welding. One thermocouple was passed through the intestine wall in order to be in contact with the bottom part of the solder strip. The two thermocouple (temperature range from −204 to 404° C., diameter=0.5 mm, response time=0.1 s) were fixed on the opposite sides of the strip and the laser irradiated the top solder surface without shining on the thermocouple. Each thermocouple was connected to a multimeter, which displayed the solder temperatures. Both thermocouples recorded 22±1° C. prior to laser irradiation. The strip was irradiated for 30 s and its temperatures were recorded every 10 s. The irradiation time was decreased with respect to the previous laser solder welds as approximately one third of the solder surface was occupied by the thermocouple set up.

The difference between the external solder temperature and the tissue-solder interface was significantly lower (p<0.05) for the TL solder (approximately 6° C.) than for the OL solder (approximately 15° C.). Therefore, the two layer solder method can be used to measure the solder-tissue temperature during welding.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A composition for tissue welding comprising an active compound, a physiologically compatible solvent, and an energy converter, wherein said active compound is present in said composition in a concentration greater than 70% w/w such that said composition is insoluble in physiological fluids.

2. The composition of claim 1, wherein said composition is homogenized.

3. The composition of claim 1, wherein said active compound is a protein or a peptide.

4. The composition of claim 3, wherein said active compound is selected from the group consisting of albumin, collagen, myoglobin, and fibrinogen.

5. The composition of claim 4, wherein said active compound is albumin.

6. The composition of claim 1, wherein said energy converter is selected from the group consisting of carbon black, india ink, fluorescein, and indocyanine green.

7. The composition of claim 6, wherein said energy converter is carbon black.

8. The composition of claim 7, wherein said carbon black is present in a concentration of about 0.15% to about 0.25% (w/w).

9. The composition of claim 1, wherein said solvent and said energy converter are the same.

10. The composition of claim 9, wherein said solvent and energy converter are $D_2O$.

11. The composition of claim 1, wherein said composition further comprises at least one bioactive agent.

12. The composition of claim 1, wherein said composition is preformed into a shape.

13. The composition of claim 12, wherein said shape is a cylinder.

14. A composition comprising multiple compositions according to claim 1, wherein said multiple compositions may or may not comprise the same active compound, solvent and energy converter.

15. The composition of claim 14, wherein said composition comprises multiple layers.

* * * * *